United States Patent [19]

Tonne et al.

[11] 4,421,931
[45] Dec. 20, 1983

[54] PREPARATION OF ANTHRANILIC ACID AMIDES

[75] Inventors: Peter Tonne, Neustadt; Winfried Ludwig, Gruenstadt; Gerhard Kilpper, Carlsberg; Johannes Grimmer, Ludwigshafen, all of Fed. Rep. of Germany

[73] Assignee: BASF Aktiengesellschaft, Fed. Rep. of Germany

[21] Appl. No.: 338,243

[22] Filed: Jan. 11, 1982

[30] Foreign Application Priority Data

Feb. 3, 1981 [DE] Fed. Rep. of Germany ....... 3103563

[51] Int. Cl.$^3$ ................ C07C 102/04; C07C 103/28; C07C 103/76
[52] U.S. Cl. ................................. 564/139; 564/163; 564/167; 564/168
[58] Field of Search ................ 564/139, 163, 167, 168

[56] References Cited

U.S. PATENT DOCUMENTS

| 3,409,668 | 11/1968 | Palazzo et al. | 564/163 |
| 4,093,734 | 6/1978 | Krüger et al. | 564/163 X |
| 4,177,041 | 12/1979 | Sung et al. | 564/163 X |
| 4,191,706 | 3/1980 | Marquis et al. | 564/163 X |

FOREIGN PATENT DOCUMENTS

| 1543332 | 8/1969 | Fed. Rep. of Germany . |
| 2129200 | 6/1971 | Fed. Rep. of Germany . |
| 2400111 | 7/1975 | Fed. Rep. of Germany . |
| 2719020 | 4/1977 | Fed. Rep. of Germany . |

OTHER PUBLICATIONS

J. Amer. Chem. Soc. 88 (1966), pp. 4001–4008.
J. Prakt. Chem. 30 (1884) [2], pp. 467–483.
J. Org. Chem. 24 (1959), pp. 1214–1219.
J. Org. Chem. 3 (1938), pp. 414–423.
J. Org. Chem. 12 (1947), pp. 743–751.
J. Org. Chem. 26 (1961), pp. 613–614.
Tonne et al., EP 57-424, Aug. 1982.
Fifolt et al., EP 55-630, Jul. 1982.
Wagner & Zook, *Synthetic Organic Chemistry*, pp. 567, 674–675, John Wiley & Sons, Inc., N.Y.

*Primary Examiner*—Thomas A. Waltz
*Attorney, Agent, or Firm*—Keil & Witherspoon

[57] ABSTRACT

Anthranilic acid amides are prepared by mixing phthalamic acid with a caustic alkali solution, a catalyst and a hypohalite, allowing the mixture to stand for from 1 to 1,000 seconds, then introducing the amine and thereafter addig acid until the pH of the mixture is from 6 to 8.

The anthranilic acid amides obtainable by the process of the invention are valuable starting materials for the preparation of dyes, scents and pesticides.

13 Claims, No Drawings

PREPARATION OF ANTHRANILIC ACID AMIDES

The present invention relates to a novel process for the preparation of anthranilic acid amides by mixing phthalamic acid with a caustic alkali solution, a catalyst and a hypohalite, allowing the mixture to stand for from 1 to 1,000 seconds, then introducing the amine and thereafter adding acid until the pH of the mixture is from 6 to 8.

Preparation processes based on the reaction of isatoic anhydride with amines are known.

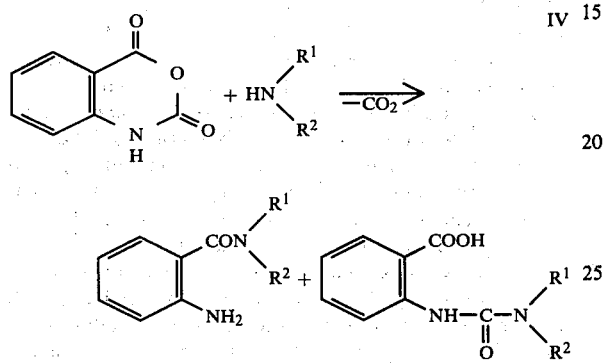

However, these processes give, in addition to the desired anthranilic acid amides, considerable quantities of urea derivatives IV as by-products, and these reduce the yield and make subsequent purification operations necessary (J. Am. Chem. Soc. 88 (1966), 4001–4008).

It is reported in J. prakt. Chem., 30 (1884), [2], 467 et seq. and in J. org. Chem. 13 (1948), 347 et seq. and 24 (1959), 1214 et seq. that isatoic anhydride reacts with aqueous ammonia to give anthranilic acid amide and o-ureidobenzoic acid. The reaction of 5,7-dichloroisatoic anhydride with ammonia leads to 6,8-dichlorobenzoylurea (J. org. Chem . 3 (1938), 414 et seq. and 12 (1947), 743), whilst other chlorine-substituted isatoic anhydrides give only moderate yields of chlorinated anthranilic acid amides (J. org. Chem. 26 (1961) 613 et seq.). A corresponding reaction of 6-nitroisatoic anhydride, as described in J. prakt. Chem., 30 (1884), [2], 467 et seq., gives 5-nitroanthranilic acid amide in poor yield and purity. It was only possible to establish a decomposition point for the resulting end product, and this lay about 30° C. below the melting point of the pure end product. The product is apparently contaminated by nitroureidobenzoic acid and can be separated off and purified only by a complicated procedure, for example by salt formation with hydrochloric acid or sulfuric acid and subsequent precipitation with alkali metal hydroxide solution; this process is therefore unsuitable, particularly for a large-scale industrial preparation.

Numerous attempts have therefore been made to improve the yield of the amides. According to German Laid-Open Application DOS No. 1,543,332, the reaction is preferably carried out in a water-miscible organic solvent. This process has the disadvantage that to isolate the anthranilic acid amide in a further process step either the solvent has to be distilled off or water has to be added, thereby leading to a loss of the solvent used. The isatoic anhydride and the amine are added to the solvent simultaneously and in stoichiometric amounts.

J. Am. Chem. Soc. 88 (1966), 4001, investigates several examples of the kinetics of reaction of isatoic anhydride with amines. According to this paper, it is advantageous to carry out the reaction at high dilution (up to $10^{-3}$ M) in order to obtain good yields of amides. Furthermore, relatively high amine concentrations promote the formation of the urea acids IV. Therefore, amine hydrochlorides and certain amounts of sodium chloride are added; moreover, in some cases a very large excess of amine/amine hydrochloride (in some cases more than 1 to 10) is used. For these reasons, the process is not practicable on an industrial scale.

German Laid-Open Application DOS No. 2,719,020 describes the reaction of isatoic anhydride with amines, advantageously in a pH range of from 7 to 10.5, buffer systems of amine hydrochlorides and amine carbonates advantageously being used to establish the pH. This process has the disadvantage that mixtures of an amine, an amine hydrochloride and an amine carbonate are used, which have to be prepared in an upstream stage.

We have found that anthranilic acid amides of the formula

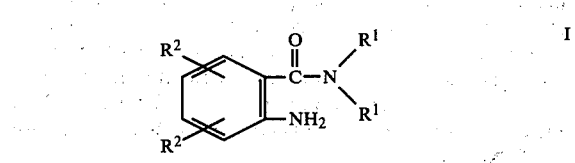

where the individual radicals $R^1$ and $R^2$ can be identical or different and each is hydrogen or an aliphatic radical, $R^1$ can also be a cycloaliphatic, araliphatic or aromatic radical and $R^2$ can also be halogen or alkoxy, are advantageously obtained if a phthalamic acid of the formula

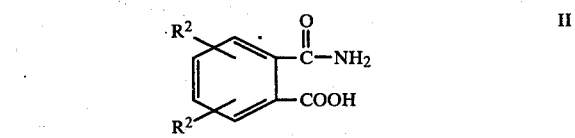

where $R^2$ has the above meaning, is reacted with a hypohalite and ammonia or an amine of the formula

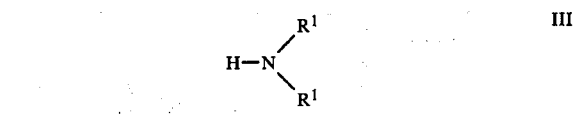

where $R^1$ has the above meaning, by dissolving the starting material II in aqueous alkali, mixing the solution with amidosulfonic acid, sulfamide and/or potassium iodide as the catalyst and a hypohalite, leaving the mixture to stand for from 1 to 1,000 seconds, then introducing the amine and thereafter adding acid until the pH of the mixture is from 6 to 8.

If phthalamic acid, ammonia, sodium hydroxide solution and sodium hypochlorite are used, the reaction can be represented by the following equation:

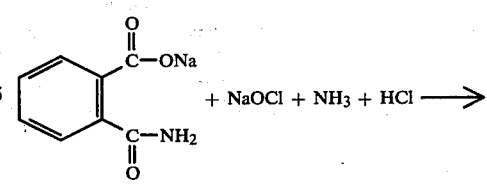

-continued

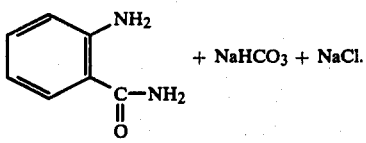
+ NaHCO₃ + NaCl.

Compared to the known processes, the process according to the invention gives anthranilic acid amides by a simpler and more economical route, in better yield and purity, and permits the preparation of a large number of amines with alkali metal hypohalite solutions, even on a large-industrial scale. Since the alkaline hypochlorite solution is more stable than the hypobromite solution and its strength hardly decreases even after days, the novel process is safer to operate, is freer from breakdowns and is particularly suitable for industrial operation. Compared to the known processes which use hypochloride solutions, for example for the preparation of aromatic amines, the novel process gives better overall results with respect to yield or purity of the end product. In view of the prior art, the advantageous results of the process according to the invention are surprising, since it is known that when carboxamides are reacted with hypohalites with the addition of amines, the corresponding ureas are formed in high yield; see, for example, German Laid-Open Application DOS No. 2,400,111

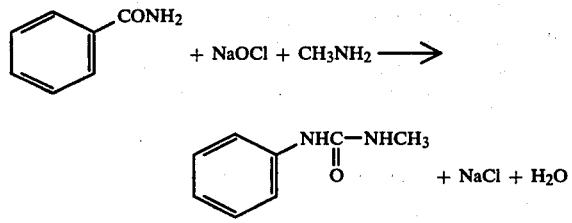

or German Laid-Open Application DOS 2,129,200

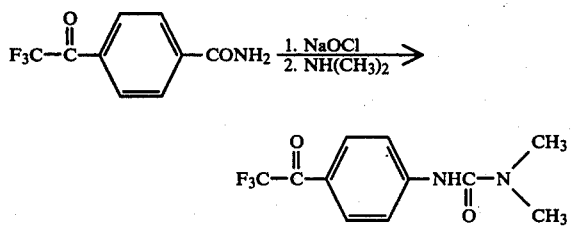

In general, ammonia is added in the form of an aqueous solution of preferably from 1 to 25 percent strength by weight, and the starting materials II and III are introduced in liquid form or as aqueous suspensions.

Preferred phthalamic acids II and amines III and, correspondingly, preferred anthranilic acid amides I, are those in whose formulae the individual radicals $R^1$ and $R^2$ can be identical or different and each is hydrogen or alkyl of 1 to 10, in particular 1 to 4, carbon atoms, $R^1$ can also be cyclohexyl, aralkyl or alkylaryl of 7 to 12 carbon atoms, phenyl, benzoylphenyl or naphthyl, and $R^2$ can also be bromine or chlorine, or alkoxy of 1 to 4 carbon atoms. The above radicals can also be substituted by groups and/or atoms which are inert under the reaction conditions, for example substituted in the benzene nucleus by chlorine, bromine or alkoxy of 1 to 4 carbon atoms, alkyl of 1 to 4 carbon atoms and nitro.

The following phthalamic acids are examples of suitable starting materials II: phthalamic acid and phthalamic acids which are monosubstituted in the 4-, 5-, 6- and 7-position by chlorine, bromine, methoxy, ethoxy, propoxy, isopropoxy, butoxy, isobutoxy, sec.-butoxy, tert.-butoxy, pentoxy, methyl, ethyl, propyl, isopropyl, butyl, isobutyl, sec.-butyl, tert.-butyl, pentyl, hexyl or hexoxy.

Examples of suitable starting materials III are dimethylamine, diethylamine, dipropylamine, diisopropylamine, dibutylamine, diisobutylamine, ammonia, di-sec.-butylamine, di-tert.-butylamine, debenzylamine, dicyclohexylamine, diamylamine, dihexylamine, N-methylaniline, N-ethylaniline, N-propylaniline, N-methyltoluidine, N-ethyltoluidine, N-propyltoluidine, N-methylaminoethanol, N-ethylaminoethanol, N-propylaminoethanol, N,N'-dimethylethylenediamine, N,N'-diethylethylenediamine, N-methylcyclohexylamine, methylamine, ethylamine, propylamine, isopropylamine, butylamine, sec.-butylamine, tert.-butylamine, benzylamine, hexylamine, cyclohexylamine, amylamine aniline, toluidine and aminoethanol.

Further starting materials used are hypohalites, advantageously hypochlorites in aqueous medium, as a rule in the form of appropriate aqueous alkaline solutions. The starting material II is advantageously used as an aqueous suspension of from 1 to 50% strength by weight. The aqueous hypochlorite solutions contain in general from 5 to 15, preferably from 12 to 14, % by weight of hypochlorite and can in addition contain up to 0.2 mole of alkali metal hydroxide per mole of hypochlorite. The mixture of the two starting materials generally contains a total of from 0.9 to 1.5, preferably from 0.95 to 1.1, moles of hypochlorite and advantageously a total of from 1.0 to 1.5 moles, preferably from 1.0 to 1.2 moles of alkali metal hydroxide (not including the alkali metal contained in the hypochlorite) per mole of starting material II. Sodium hypochlorite and potassium hypochlorite are preferred.

As a rule, the reaction is carried out at from −10° C. to +100° C., preferably from 10 to 85° C., under atmospheric or superatmospheric pressure and continuously or batchwise. The reaction can be carried out as follows: starting material II is dissolved in an aqueous caustic alkali, preferably sodium hydroxide solution or potassium hydroxide solution, advantageously in a 1 to 50 percent strength by weight aqueous caustic alkali solution. The catalyst is advantageously added during the preparation of the solution. From 0.001 to 0.2, in particular from 0.01 to 0.1, mole of catalyst per mole of alkali metal hydroxide is advantageously used. Aqueous sodium hypohalite is then added. The residence time from the end of the preparation of the starting mixture, when all components have been added completely, to the beginning of the addition of the amine III is from 1 to 1,000, preferably from 1 to 100, seconds, and the residence time from the end of the preparation of the starting mixture to the beginning of the addition of the acid is from 1 to 1,000, preferably from 1 to 100, seconds. It is advantageous to choose a residence time of from 1 to 100, preferably from 1 to 10, seconds from the end of the amine addition to the beginning of the acid addition.

The starting materials can be reacted in stoichiometric amounts or in excess, advantageously in a ratio of from 1.0 to 1.5, preferably from 1.1 to 1.5, moles of starting material III per mole of starting material II. From 1.0 to 1.6, in particular from 1.4 to 1.5, equivalents of acid per mole of starting material II are advantageously used. Inorganic or organic acids can be used, and it is possible to employ equivalent quantities of polybasic acids instead of monobasic acids. The following are examples of suitable acids: hydrogen chloride, hydrogen bromide, hydrogen iodide, sulfuric acid, phosphoric acid, carbonic acid, formic acid, acetic acid and 2-ethylhexanoic acid. The acids can be used in concentrated form, as a mixture with one another and/or as a mixture with a solvent, particularly water. It is advantageous to use dilute aqueous acids of from 1 to 98 percent strength by weight, for example 10 to 30 percent strength by weight hydrochloric acid, 10 to 50, preferably 20 to 30, percent strength by weight sulfuric acid or 70 to 85 percent strength by weight formic acid. Hydrochloric acid, sulfuric acid, phosphoric acid and formic acid are preferred. The reaction is carried out at a pH of from 6 to 8, preferably from 6.4 to 7.6, in particular from 6.7 to 7.3.

The end product I is isolated from the reaction mixture in a conventional manner, for example by filtration and fractional distillation. The precipitated anthranilic acid amides I can be directly filtered off under suction and the mother liquor can be recycled to the process. The yields of the amides I are from 80 to 95% of theory and the purity is 99%, determined by diazotization.

For certain intended uses, it is advantageous to employ the amides in the presence of a water-immiscible solvent instead of isolating them in solid form, and for this purpose an organic solvent is metered in simultaneously with the addition of the amine. Particularly suitable solvents for this purpose are 1,2-dichloroethane, dichloroethylene, 1,2-dichloropropane, chlorobenzene and dichlorobenzene. The novel process is particularly advantageously carried out in a continuous manner. For this purpose, the phthalamic acid solution prepared by hydrolysis of phthalimide with NaOH is continuously reacted with hypohalites in a mixing apparatus. After residence times of from 1 to 30 seconds, the amine, the mineral acid and the organic solvent are simultaneously added, a pH of from 6 to 8 is maintained and, after residence times of from 1 to 60 minutes at temperatures of from 20° to 80° C., the organic phase is separated from the aqueous phase and is processed further.

The anthranilic acid amides I obtainable by the process of the invention are valuable starting materials for the preparation of dyes, scents and pesticides. Thus, it is possible to obtain 2-aminobenzonitriles, which are valuable intermediates for the preparation of azo dyes, for example by reacting the above starting materials with agents which split off water. Regarding the use of these compounds, reference may be made to Ullmanns Encyklopädie der technischen Chemie, volume 3, pages 310 and 465 et seq. and volume 19, pages 300 et seq., and to the above publications.

In the Examples which follow, parts are by weight and are related to parts by volume as kilogram to liter.

EXAMPLE 1

42 parts per hour of liquid phthalimide are dissolved continuously in 48 parts of 25 percent strength by weight aqueous sodium hydroxide solution and 400 parts of water in a mixing apparatus, and one part per hour of a 30 percent strength by weight aqueous solution of sodium aminosulfonate is continuously metered into the mixture at 25° C.

This reaction mixture is mixed, in a mixing nozzle, with 155 parts of aqueous sodium hypochlorite solution (13.6% by weight of active chlorine, 21 parts of sodium hypochlorite) and 170 parts of $H_2O$ at 25° C.

After a residence time of 3 seconds in a tube reactor, 25 parts per hour of isopropylamine are then introduced via a mixing nozzle and, after a further second, 40 parts of a 30 percent strength by weight aqueous hydrochloric acid solution (pH 6.9) are introduced via a third mixing apparatus.

After a total residence time of 4 seconds at 30° C. in the tube reactor, the reaction mixture flows into a stirred vessel (delay vessel) into which 235 parts per hour of dichloroethane run, and at the same time the pH is kept constant at 6.9 by the addition of a further 10 parts of 30 percent strength by weight aqueous hydrochloric acid. The temperature in the delay vessel is 60° C.

After a residence time of 10 minutes in the delay vessel, the organic phase is continuously separated off, in a separation apparatus, from the aqueous phase and is processed further.

46 parts per hour of anthranilic acid isopropylamide are obtained as a 12 percent strength by weight solution in dichloroethane (90.5% of theory). The solidification point is 149° C. and the purity is 99.3%, determined by diazotization. The space-time yield is 0.2 parts per hour per liter.

EXAMPLE 2

The reaction is carried out similarly to Example 1 but instead of using dichloroethane as the solvent, 320 parts per hour of dichloropropane are employed, the temperature in the delay vessel is kept constant at 60° C. and the residence time is reduced to 4 minutes as compared with 10 minutes in Example 1. The residence time from the end of the preparation of the starting mixture to the beginning of the addition of the ammonia/amine is 3 seconds and to the beginning of the addition of acid is 4 seconds.

45 parts per hour of anthranilic acid isopropylamide (89% of theory) are obtained in 99% purity, determined by diazotization. The space-time yield is 0.37 parts per hour and liter and the melting point is 149° C.

EXAMPLE 3

42 parts of phthalimide, 48 parts of 25 percent strength by weight aqueous sodium hydroxide solution, 400 parts of water, one part of a 30 percent strength by weight aqueous solution of sodium aminosulfonate and 149 parts of aqueous sodium hypochlorite solution (13.6% by weight of active chlorine) are reacted similarly to Example 1.

Instead of isopropylamine, 20 parts per hour of a 25 percent strength by weight aqueous ammonia solution are admixed and 40 parts of a 30 percent strength by weight aqueous hydrochloric acid solution are added at 50° C. The residence time from the end of the preparation of the starting mixture to the beginning of the addition of ammonia is 15 seconds and to the beginning of the addition of acid is 35 seconds.

After a total residence time of 40 seconds, the reaction mixture flows into a delay vessel in which the pH is kept constant at 6.9 by the addition of a further 12 parts of 30 percent strength by weight aqueous hydrochloric acid. The temperature in the delay vessel is 50°

C. After a residence time of 13 minutes, the anthranilic acid amide formed is extracted from the aqueous solution with dichloroethane in an extraction column and is processed further.

34 parts per hour of anthranilic acid amide (84% of theory), of melting point of 110° C., are obtained in 99.5% purity, determined by diazotization.

EXAMPLE 4

21.6 parts of 4-chlorophthalamic acid are dissolved in 100 parts of water and 17 parts of 25 percent strength by weight aqueous sodium hydroxide solution and 0.1 part of potassium iodide is added. The solution is cooled to 15° C. and 57 parts of an aqueous sodium hypochlorite solution, containing 8.0 parts of sodium hypochlorite, also at 15° C., are added.

After 30 seconds, 9 parts of isopropylamine and 8 parts of a 30 percent strength by weight and aqueous hydrochloric acid are added to the mixture and the pH is kept constant at 7.0 by the addition of further hydrochloric acid. The residence time from the end of the preparation of the starting mixture to the beginning of the addition of the amine is 30 seconds and to the beginning of the addition of acid is 31 seconds. The mixture is stirred at 30° C. for a total of half an hour, and is filtered and dried.

The yield, which corresponds to 82% of theory, is 17 parts of 4-chloroanthranilic acid isopropylamide, of a melting point of 168°–170° C.

We claim:

1. A process for the preparation of an anthranilic acid amide of the formula

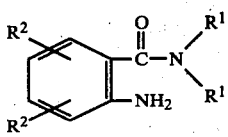

where the individual radicals $R^1$ and $R^2$ can be identical or different and each is hydrogen or an aliphatic radical, $R^1$ can also be cycloaliphatic, araliphatic or aromatic radical and $R^2$ can also be halogen or alkoxy, wherein a phthalamic acid of the formula

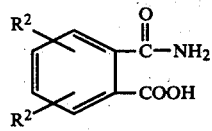

where $R^2$ has the above meaning, is reacted with a hypohalite and ammonia or an amine of the formula

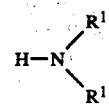

where $R^1$ has the above meaning, by dissolving the starting material II in aqueous alkali, mixing the solution with amidosulfonic acid, sulfamide and/or potassium iodide as a catalyst and a hypohalite, leaving the mixture to stand for from 1 to 1,000 seconds, then introducing the amine and thereafter adding acid until the pH of the mixture is from 6 to 8.

2. A process as claimed in claim 1, wherein the reaction is carried out using aqueous suspensions of from 1 to 50% by weight of starting material II.

3. A process as claimed in claim 1, wherein the reaction is carried out using from 0.9 to 1.5 moles of hypochlorite per mole of starting material II.

4. A process as claimed in claim 1, wherein the reaction is carried out using from 1.0 to 1.5 moles of alkali metal hydroxide (not including the alkali metal contained in the hypochlorite) per mole of starting material II.

5. A process as claimed in claim 1, wherein the reaction is carried out at from −10° to +100° C.

6. A process as claimed in claim 1, wherein the reaction is carried out at from 10° to 85° C.

7. A process as claimed in claim 1, wherein the reaction is carried out using a molar ratio of from 0.001 to 0.2 mole of catalyst per mole of alkali metal hydroxide.

8. A process as claimed in claim 1, wherein the reaction is carried out with a residence time of from 1 to 100 seconds from the end of the preparation of the starting mixture, when all components have been added completely, to the beginning of the addition of amine III.

9. A process as claimed in claim 1, wherein the reaction is carried out with a residence time of from 1 to 100 seconds from the end of the preparation of the starting mixture to the beginning of the addition of acid.

10. A process as claimed in claim 1, wherein the reaction is carried out using from 1.0 to 1.5 moles of starting material III per mole of starting material II.

11. A process as claimed in claim 1, wherein the reaction is carried out using from 1.0 to 1.6 equivalents of acid per mole of starting material II.

12. A process as claimed in claim 1, wherein the reaction is carried out at a pH of from 6.4 to 7.6.

13. A process as claimed in claim 1, wherein the reaction is carried out in the presence of a water-immiscible solvent.

* * * * *

UNITED STATES PATENT AND TRADEMARK OFFICE
CERTIFICATE OF CORRECTION

PATENT NO. :  4,421,931

DATED :  December 20, 1983

INVENTOR(S) :  Peter TONNE et al.

It is certified that error appears in the above-identified patent and that said Letters Patent is hereby corrected as shown below:

IN THE ABSTRACT:

Line 5, "addig" should be --adding--.

Signed and Sealed this

Seventeenth Day of April 1984

[SEAL]

Attest:

GERALD J. MOSSINGHOFF

Attesting Officer   Commissioner of Patents and Trademarks